United States Patent [19]

Brown et al.

[11] Patent Number: 4,822,815
[45] Date of Patent: Apr. 18, 1989

[54] DIOXANE HEXENOIC ACIDS

[75] Inventors: George R. Brown, Wilmslow; Michael J. Smithers, Macclesfield, both of United Kingdom

[73] Assignee: Imperial Chemical Industries PLC, London, England

[21] Appl. No.: 940,076

[22] Filed: Dec. 10, 1986

[30] Foreign Application Priority Data

Dec. 30, 1985 [GB] United Kingdom ............... 8531892

[51] Int. Cl.$^4$ ................ A61K 31/38; C07D 409/00
[52] U.S. Cl. ............................ 514/444; 514/452; 549/60; 549/350; 549/370; 549/373; 549/375
[58] Field of Search ............ 549/370, 373, 375, 350, 549/60; 514/444, 452

[56] References Cited

U.S. PATENT DOCUMENTS

| | | | |
|---|---|---|---|
| 2,500,155 | 3/1950 | Croxall | 549/375 |
| 2,992,234 | 7/1961 | Acker | 549/375 |
| 4,085,222 | 4/1978 | Rhodes et al. | 549/60 |
| 4,567,197 | 1/1986 | Brewster et al. | 549/373 |
| 4,668,698 | 5/1987 | Brewster | 549/350 |

FOREIGN PATENT DOCUMENTS 0094239 11/1983 European Pat. Off.
43-3392 2/1968 Japan ........................... 549/375

Primary Examiner—Alan Siegel
Attorney, Agent, or Firm—Cushman, Darby & Cushman

[57] ABSTRACT

The invention concerns novel 1,3-dioxane hexenoic aids and related carboxytic acid esters and alkanesulphonamides of the formula I in which X is oxy or thio, $R^1$ is hydrogen, halogeno, trifluoromethyl, cyano or nitro and $R^2$ is hydrogen, together with their pharmaceutically acceptable salts. The invention also concerns processes for the production of the novel compounds and pharmaceutical compositions containing the compounds for use in the treatment of various diseases in which thromboxane $A_2$ ($TXA_2$) is implicated.

11 Claims, No Drawings

DIOXANE HEXENOIC ACIDS

This invention concerns novel dioxane hexenoic acids and, more particularly, novel 4(Z)-6-([2,4,5-cis]-2-heterocyclyl-4-phenyl-1,3-dioxan-5-yl)-acids and related derivatives which antagonise one or more of the actions of thromboxane $A_2$ (hereafter referred to as "$TXA_2$") and which are of value as therapeutic agents.

It is known that $TXA_2$ is a potent aggregator of blood platelets and a powerful vasoconstrictor. $TXA_2$ is also a potent constrictor of bronchial and tracheal smooth muscle. $TXA_2$ may therefore be involved in a wide variety of disease conditions, for example ischaemic heart disease such as myocardial infarction, angina, cerebrovascular disease such as transient cerebral ischaemia, migraine and stroke, peripheral vascular disease such as atherosclerosis, microangiopathy, hypertension and blood clotting defects due to lipid imbalance, and pulmonary disease such as pulmonary embolism, bronchial asthma, bronchitis, pneumonia, dyspnoea and emphysema. Accordingly, compounds which antagonise the actions of $TXA_2$ may be expected to have therapeutic value in the prevention or treatment of any one or more of the above mentioned diseases or any other disease conditions in which it is desirable to antagonise the actions of $TXA_2$.

It is also known from our European patent application, publication number 94239, that 4-phenyl1,3-dioxan-5-ylalkenoic acid derivatives of the formula Z having cis-relative stereochemistry at positions 4 and 5 of the dioxane ring and wherein Ra and Rb are variously hydrogen, alkyl, halogenoalkyl, alkenyl and optionally substituted aryl or arylalkyl, Rc is hydroxy, alkoxy or alkanesulphonamido, n is 1 or 2, A is ethylene or vinylene, Y is (2–5C)polymethylene optionally substituted by alkyl and benzene ring B bears one or two optional substituents, possess the property of antagonising one or more of the actions of $TXA_2$. We have now discovered and herein lies the basis of our invention that particularly useful $TXA_2$ antagonism in shown by a novel group of compounds of formula Z in which Ra is replaced by optionally substituted furyl or thienyl, Rb is hydrogen, benzene ring B is o-hydroxyphenyl, n is 1, A is cis-vinylene, Y is ethylene and Rc is hydroxy.

According to the invention there is provided a 1,3-dioxane hexenoic acid of the formula I set out hereinafter wherein X is oxy or thio; $R^1$ is selected from hydrogen, halogeno, trifluoromethyl, cyano, and nitro; $R^2$ is hydrogen; and wherein the groups at positions 2, 4 and 5 of the 1,3-dioxane ring have cis-relative stereochemistry; or a biodegradable ester or a (1–6C)alkanesulphonamide thereof; or a pharmaceutically acceptable salt thereof.

It will be appreciated that the compounds of formula I possess asymmetric carbon atoms and may exist and be isolated in racemic and optically active forms. The invention includes both the racemic forms and any optically active form (or mixtures thereof) which is capable of antagonising one or more of the actions of $TXA_2$, it being well known in the art how to prepare individual optical isomers (for example by synthesis from optically active starting materials or resolution of a racemic form) and how to determine the $TXA_2$ antagonist properties using one or more of the standard tests referred to hereafter.

In the chemical formulae attached hereto, although a particular configuration is shown, this does not necessarily correspond to the absolute configuration.

A particular value for $R^1$ when it is halogeno is, for example, fluoro, chloro or bromo.

A preferred value for $R^1$ is, for example, hydrogen, chloro, bromo, nitro or cyano, and more especially when it is located on the carbon atom adjacent to the hetero atom X.

A particular value for the hetero cyclyl group containing X and bearing substituent $R^1$ is, for example, 2-furyl, 3-furyl, 2-thienyl, 3-thienyl, 5-bromo-2-thienyl, 5-nitro-2-furyl, 5-nitro-2-thienyl, 5-nitro-3-thienyl or 5-bromo-3-thienyl or 5-cyano-2-thienyl.

A preferred group of compounds of the invention comprises the compounds of formula VII wherein Z is selected from hydrogen, nitro, halogeno (especially bromo) and cyano; X is oxy or thio; and the groups at positions 2,4 and 5 of the 1,3-dioxane ring have cis-relative stereochemistry; or a biodegradable ester or a (1–6C)alkanesulphonamide thereof; or a pharmaceutically acceptable salt thereof.

Specific compounds of particular interest are set out in the accompanying Examples. Of these the compounds described in Examples 4, 8 and 9 are especially potent antagonists of one or more of the actions of $TXA_2$.

Particular pharmaceutically acceptable salts of acids or sulphonamides of formula I are, for example, alkali metal and alkaline earth metal salts such as lithium, sodium, potassium, magnesium and calciu salts, aluminum and ammonium salts, and salts with organic amines and quaternary bases forming physiologically acceptable cations such as salts with methylamine, dimethylamine, trimethylamine, ethylenediamine, piperidine, morpholine, pyrrolidine, piperazine, ethanolamine, triethanolamine, N-methylglucamine, tetramethylammonium hydroxide and benzyltrimethylammonium hydroxide.

Particular biodegradable esters of acids of formula I include, for example, (1–4C)alkyl esters (such as methyl and ethyl esters), phenyl and benzyl esters.

Particular (1–6C)alkanesulphonamides of acids of formula I include, for example, the methanesulphonamides, ethanesulphonamides and 1-methylethanesulphonamides.

The compounds of formula I may be manufactured by conventional procedures of organic chemistry, well known in the art for the manufacture of structurally analogous compounds. Such procedures are provided as a further aspect of the invention and are illustrated by the following processes in which X, $R^1$ and $R^2$ have any of the meanings defined hereinabove:

(a) An aldehyde of the formula II is reacted with a Wittig reagent of the formula $R_3P=CH(CH_2)_2CO_2^-M^+$ wherein R is (1–6C)alkyl or aryl (especially phenyl) and $M^+$ is a cation, for example an alkali metal cation such as the lithium, sodium or potassium cation.

The process in general produces the required compounds of formula I in which the substituents adjacent to the double bond have predominantly cis-relative stereochemistry i.e. the "Z" isomer. However the process also produces analogous compounds having trans-relative stereochemistry which may be removed by a conventional procedure such as chromatography or crystallisation.

The process is conveniently performed in a suitable solvent or diluent, for example an aromatic solvent such as benzene, toluene or chlorobenzene, an ether such as 1,2-dimethoxyethane, t-butyl methyl ether, dibutyl ether or tetrahydrofuran, in dimethyl sulphoxide or tetramethylene sulphone, or in a mixture of one or more such solvents or diluents. The process is generally performed at a temperature in the range, for example, −80° C. to 40° C., but is conveniently performed at or near room temperature, for example in the range 0° to 35° C.

(b) A phenol derivative of the formula III wherein $R^3$ is a suitable protecting group, for example (1–6C)alkyl (such as methyl or ethyl), acyl (such as acetyl, benzoyl, methanesulphonyl or p-toluenesulphonyl) or trimethylsilyl, is deprotected.

The deprotection conditions used depend on the nature of the protecting group $R^3$. Thus, for example, when it is methyl or ethyl the deprotection may be carried out by heating with sodium thioethoxide in a suitable solvent (such as N,N-dimethylformamide or N,N-dimethyl-3,4,5,6-tetrahydro-2(1H)-pyrimidinone) at a temperature in the range, for example, 50° to 160° C. Alternatively, an ethyl or methyl protecting group may be removed by reaction with lithium diphenylphosphide in a suitable solvent (such as tetrahydrofuran or methyl t-butyl ether) at a temperature in the range, for example, 0° to 60° C. When the protecting group is acyl it may be removed, for example, by hydrolysis in the presence of a base (such as sodium or potassium hydroxide) in a suitable aqueous solvent [such as an aqueous (1–4C)alkanol] at a temperature in the range, for example, 0° to 60° C. When the protecting group is trimethylsilyl, it may be removed, for example, by reaction with aqueous tetrabutylammonium fluoride or sodium fluoride using a conventional procedure.

(c) An erythro-diol derivative of the formula IV wherein one of $Q^1$ and $Q^2$ is hydrogen and the other is hydrogen or a group of the formula —CRaRb.OH (wherein Ra and Rb are the same or different alkyl) is reacted with a heterocyclic aldehyde of the formula V or with an acetal, hemiacetal or hydrate thereof.

The aldehyde V [or its hydrate, or its acetal or hemiacetal with a (1–4C)alkanol (such as methanol or ethanol)] may conveniently be present in an excess.

The reaction is generally performed in the presence of an acid catalyst such as hydrogen chloride, hydrogen bromide, sulphuric acid, phosphoric acid, methanesulphonic acid or p-toluenesulphonic acid, conveniently in the presence of a suitable solvent or diluent, such as toluene, xylene or an ether, for example tetrahydrofuran, dibutyl ether, methyl t-butyl ether or 1,2-dimethoxyethane, and at temperature in the range, for example 0° to 80° C.

Those starting materials of formula IV wherein $Q^1$ and $Q^2$ and both hydrogen may be obtained, for example by mild, acid catalysed, hydrolysis or alcoholysis of the dioxane ring of a compound of formula VI wherein Ra and Rb are both alkyl such as methyl or ethyl, obtained by an analogous procedure to process (a) herein. The hydrolysis or alcoholysis will normally be carried out at a temperature in range 10° to 80° C. using an aqueous mineral acid such as hydrochloric acid in an alkanol, such as ethanol or 2-propanol, or an ether (such as tetrahydrofuran) as solvent.

The starting materials of formula IV wherein one of $Q^1$ and $Q^2$ is hydrogen and the other is a group of the formula —CRaRb.OH are intermediates in the abovementioned formation of the starting materials of formula IV wherein $Q^1$ and $Q^2$ are both hydrogen. However, said intermediates are not normally isolated or characterised. Accordingly, the invention also provides a process (d) which is a modification of process (c) which comprises reacting a compound of formula VI wherein one of Ra and Rb is hydrogen, methyl or ethyl and the other is methyl or ethyl with an excess of a heterocyclic aldehyde of the formula V (or of a hydrate, acetal or hemiacetal thereof) in the presence of an acid catalyst (such as one of those given above), conveniently at a temperature in the range, for example, 10° to 80° C. and optionally in the presence of a suitable solvent or diluent (such as one of those given above).

The starting materials for use in the above processes may be made by general procedures of organic chemistry, known for the preparation of structurally related compounds. Thus, the aldehydes of formula II may be obtained, for example, by the method shown in Scheme I. The protected phenol derivatives of formula III may be made, for example, by using an analogous procedure to process (a) above using an aldehyde analogous to that of formula II, but wherein the phenol group has been protected with the group $R^3$, such an aldehyde being made, for example, by carrying out the procedures of Scheme I omitting the deprotection step (ii). The aldehydes of formula V are in general well known in the art or may be made using methods analagous to those known in the art for other furan or thiophene carbaldehydes. Those of the starting materials of formula VI which are novel may be obtained using analogous procedures to those described in European patent application, publication No. 94239 for the corresponding heptenoic acids.

The necessary Wittig reagents may be obtained by conventional procedures, for example by treating the corresponding phosphonium halides with a strong base such as sodium hydride, lithium diisopropylamide, potassium t-butoxide or butyllithium. They are generally formed in situ just prior to carrying out the condensation process (a) above.

It will be understood that the acids of formula I may also be obtained by other conventional procedures well known in the art, for example by base catalysed hydrolysis of the corresponding esters, amides or nitriles.

When a pharmaceutically acceptable salt of a compound of formula I or its (1–6C)alkanesulphonamide is required, it may be obtained by reaction with the appropriate base affording a physiologically acceptable cation, or by any other conventional procedure.

Similarly, when an ester or (1–6C)alkanesulphonamide is required, it may be obtained by a conventional esterification or sulphonamidation procedure, for example by reaction of an acid of formula I with the appropriate alcohol or (1–6C)alkanesulphonamide in the presence of a suitable dehydrating agent, such as a carbodiimide, in a solvent such as methylene chloride and at a temperature in the range for example 10° to 50° C. Alternatively, one of the above-mentioned processes may be carried out using the appropriate ester or (1–6C)alkanesulphonamide derivatives of the previously mentioned carboxylic acid starting materials. This procedure is preferred when a (1–6C)alkanesulphonamide is required.

Further, when an optically active form of a compound of formula I is required, one of the aforesaid processes may be performed using an optically active starting material. Alternatively, the racemic form of a compound of formula I may be reacted with an optically active form of a suitable organic base, for example ephedrine, N,N,N-trimethyl(1-phenylethyl)ammonium hydroxide or 1-phenylethylamine, followed by conventional separation of the diastereoisomeric mixture of salts thus obtained, for example by fractional crystallisation from a suitable solvent, for example a (1-4C)alkanol, whereafter the optically active form of said compound of formula I may be liberated by treatment with acid using a conventional procedure for example using an aqueous mineral acid such as dilute hydrochloric acid.

Many of the intermediate defined herein are novel, for example those of formulae II, III and IV and are provided as further, separate features of the invention, and especially the acids of formula III wherein $R^3$ in (1-4C) alkyl, preferably methyl.

As stated earlier, the acids of formula I are antagonists of one or more of the actions of $TXA_2$, for example certain of its actions on blood platelets, the vasculature and/or the lung. The antagonism may be demonstrated in one or other of the following standard tests:

(a) The rabbit aortal strip model devised by Piper and Vane (*Nature*, 1969, 223, 29-35) using as agonist a freshly prepared sample of $TXA_2$, generated by addition of arachidonic acid (25 $\mu$g) to citrated, platelet rich rabbit plasma (250 $\mu$l) and allowing the mixture to aggregate fully over 90 seconds before use; alternatively the $TXA_2$ mimetic agent known as U46619 (described by R L Jones et alia in "Chemistry, Biochemistry and Pharmacological Activity of Prostanoids" edited by S M Roberts and F Scheinmann, at page 211; Pergamon Press, 1979) may be used as the agonist;

(b) A blood platelet aggregation test based on that described by Born (*Nature*, 1962, 194, 927-929) and involving:

(i) aggregating human, citrated, platelet-rich plasma by addition of the $TXA_2$ mimetic agent U46619 so that a dose-response curve is generated, (ii) generating a dose-response curve for U46619 stimulated platelet aggregation in the presence of decreasing amounts of test compound (generally in the range $10^{-5}$M to $10^{-10}$M); and (iii) calculating a $K_B$ value indicating potency of $TXA_2$ antagonism for the test compound, averaged over several concentrations, from the calculated 50% response value for U46619 aggregation in the presence and absence of test compound; and (c) a bronchoconstriction test involving measuring the inhibition by a test compound of the broncho-constriction induced in the Konzett-Rossler, anaesthetised guinea-pig model (as modified by Collier and James, *Brit.J.Pharmacol.*, 1967, 30, 283-307) by intravenous administration of the $TXA_2$ mimetic agent, U46619 and involving:

(i) obtaining a cumulative dose-response curve to U46619 induced bronchoconstriction by intravenous administration of constant volumes of increasing concentrations of U46619 (0.2-4 $\mu$g/kg) in physiological saline solution and expressing bronchoconstriction as the maximum of that theoretically obtainable with no air flow to the test animal;

(ii) generating a cumulative dose-response curve to U46619 induced bronchoconstriction at 30 minute intervals for 3 hours after oral dosing of test compound; and (iii) calculating a dose-ratio for the test compound (that is the ratio of concentration of U46619 required to cause 50% bronchoconstriction in the presence and absence of test compound) indicating the potency of $TXA_2$ antagonism.

The antagonism of the effects of $TXA_2$ on the vasculature may be demonstrated, for example in rats in the following manner:

(d) Male rats (Alderley Park strain) are anaesthetised with sodium pentobarbital and blood pressure is monitored at the carotid artery. The $TXA_2$ mimetic agent is administered intravenously via the jugular vein and an $ED_{50}$ (dose necessary to produce 50% of the maximum hypertensive effect) is established (n=3). [The $ED_{50}$ for U46619 is approximately 5 $\mu$g/kg.] A test compound is then administered either intravenously (via the jugular vein) or orally (via a cannula) directly into the stomach and the animal challenged with an $ED_{50}$ dose of U46619, five minutes after dosing with test compound and then successively every ten minutes until the hypertensive effect of U46619 is no longer blocked.

Further, the antagonism of the effects of $TXA_2$ in vivo may be demonstrated, for example, by assessing the effects of a test compound on the aggregation of blood platelets obtained after administration of test compound to a test animal, such as a rabbit, rat, guinea pig or dog, using standard procedures similar to that described in (a) above. However, when the aggregation of dog platelets is being studied it is necessary to use a predetermined, threshold concentration of the platelet aggregation agent adenosine diphosphate (about $0.4-1.2\times10^{-6}$M) together with the $TXA_2$ mimetic agent, U46619.

As an illustration, using the above test procedures (a)-(c), the following representative results hvae been obtained with the compounds of Examples 4 and 8 respectively:

Test (a), pA$_2$ (U46619) ($\pm$0.05):Ex.4, 8.3; Ex.8, 7.6;
Test (b), $K_B$:Ex.4, $7.54\times10^{-9}$M; Ex.8, $1.38\times10^{-8}$M;
Test (c), dose ratio: Ex.4, >100; Ex.8, 3 2 hours after oral dosing at 0.05 mg/kg.

Similarly, using test procedure (d) referred to above, the compounds of Example 4 described hereinafter gave about 80% inhibition of the hypertensive effect of U46619 for more than 1 hour after an oral dose of 0.05 mg/kg.

In general, other compounds of formula I and VII show similar levels of $TXA_2$ antagonist properties in one or more of the above mentioned tests e.g. test (a) PA$_2$>7.0; test (b) $K_B$:$1.0\times10^{-7}$M; test (c) dose ratio>5, 2 hours after oral dosing at 0.1 mg/kg and/or test (d), significant inhibition of U46619 induced hypertension for at least 1 hour following oral dosing at 5 mg/kg or less.

As stated previously, the acids of formula I, or a derivative or a salt thereof, as defined above, may be used in the therapy or prevention of diseases or adverse conditions in warm-blooded animals in which it is desirable to antagonise one or more of the actions of $TXA_2$. In general, an acid of formula I or a derivative or a salt thereof, will be administered for this purpose by an oral, rectal, intravenous, subcutaneous, intramuscular or inhalation route, so that a dose in the range, for example 0.01-5 mg/kg body weight, will be given up to four times per day, varying with the route of administration, the severity of the condition and the size and age of the patient under treatment.

The compounds of the invention will generally be used in the form of a pharmaceutical composition comprising a compound of formula I (or a biodegradable ester or (1-6C)alkanesulphonamide thereof; or a pharmaceutically acceptable salt thereof (as defined hereinabove)) together with a pharmaceutically acceptable diluent or carrier. Such a composition is provided as a further feature of the invention and may be in a variety of dosage forms. For example, it may be in the form of tablets, capsules, solutions or suspensions for oral administration; in the form of a suppository for rectal administration; in the form of a sterile solution or suspension for administration by intravenous or intramuscular injection; in the form of an aerosol or a nebuliser solution or suspension, for administration by inhalation; and in the form of a powder, together with pharmaceutically acceptable inert solid diluents such as lactose, for administration by insufflation.

The pharmaceutical compositions may be obtained by conventional procedures using pharmaceutically acceptable diluents and carriers well known in the art. Tablets and capsules for oral administration may conveniently be formed with an enteric coating, for example comprising cellulose acetate phthalate, to minimise contact of the active ingredient with stomach acids.

The pharmaceutical compositions of the invention may also contain in addition one or more agents known to be of value in the aforesaid diseases or conditions intended to be treated, for example a known platelet aggregation inhibitor, hypolipidemic agent, anti-hypertensive agent, beta-adrenergic blocker or a vasodilator may usefully also be present in a pharmaceutical composition of the invention for use in treating a heart or vascular disease or condition. Similarly, by way of example, an anti-histamine, steroid (such as beclomethasone dipropionate), sodium cromoglycate, phosphodiesterase inhibitor or a betaadrenergic stimulant may usefully also be present in a pharmaceutical composition of the invention for use in treating a pulmonary disease or condition. Compositions according to the invention may also comprise an inhibito for synthesis of $TXA_2$ (for example dazoxiben) in addition to one of the compounds of formula I, or a biodegradable ester or (1-6C-)alkanesulphonamide, or a pharmaceutically acceptable salt thereof, as defined hereinbefore, together with a pharmaceutically acceptable diluent or carrier.

In addition to their use in therapeutic medicine, the acids of formula I are also useful as pharmacological tools in the development and standardisation of test systems for the evaluation of the effects of $TXA_2$ in laboratory animals such as cats, dogs, rabbits, monkeys, rats and mice, as part of the search for new therapeutic agents. The acids of formula I, or the (1-6C)alkanesulphonamides thereof, or physiologically acceptable salts thereof, may also be uesd because of the $TXA_2$ antagonist properties in helping to maintain the viability of blood and blood vessels in warm-blooded animals (or parts thereof) undergoing artificial extracorporeal circulation, for example during limb or organ transplant. When used for this purpose an acid of formula I, or a physiologically acceptable salt thereof, will generally be administered so that a steady state concentration in the range, for example, 0.1 to 10mg per litre is achieved in the blood.

The invention will now be illustrated in the following non-limiting Examples in which, unless otherwise stated:

(i) evaporations were carried out by rotary evaporation in vacuo;

(ii) operations were carried out at room temperature, that is in the range 18°-26° C. and under an atmosphere of an inert gas such as argon;

(iii) flash column chromatography was performed on Merck Kieselgel (Art. 9385) obtained from E. Merck, Darmstadt, W.Germany;

(iv) yields are given for illustration only and are not necessarily the maximum attainable;

(v) proton NMR spectra were normally determined at 200 MHz in $CDCl_3$ using tetramethylsilane (TMS) as an internal standard, and are expressed as chemical shifts (delta values) in parts per million relative to TMS using conventional abbreviations for designation of major peaks: s, singlet; m, multiplet; t, triplet; br, broad; d,doublet;

(vi) all end-products were isolated as racemates.

EXAMPLE 1

2-Thiophenecarbaldehyde (0.12 ml) and p-toluene sulphonic acid (2 mg) were added to a stirred suspension of 4(Z)-6-(4-o-hydroxyphenyl-2,2-dimethyl-1,3-dioxan-cis-5-yl)hexenoic acid (A) (350 mg). The mixture was stirred for 2 hours and then purified by flash column chromatography on silica eluting with toluene-/ethyl acetate/acetic acid (91:9:2, by volume) to give 4(Z)-6-([2,4,5-cis]-4-o-hydroxy-phenyl-2-[2-thienyl]-1,3-dioxan-5-yl)hexenoic acid as a pale yellow oil (142 mg,35%) NMR: 1.78 (1H,d), 1.95 (1H,d), 2.32 (4H,m), 2.75 (1H,m), 4.18 (2H,m), 5.40 (3H,m), 5.95 (1H,s), 6.93 (4H,m), 7.24 (3H,m) and 7.69 (1H,m); m/e: 374 (M+).

The starting hexenoic acid derivative (A) was obtained as follows:

Sodium hydride (432 mg, 50% w/w dispersion in mineral oil) was added to a stirred solution of 4(Z)-6-(4-o-methoxyphenyl-2,2-dimethyl-1,3-dioxan-cis-5-yl)hexenoic acid(B) (500 mg) in 1,3-dimethyl-3,4,5,6-tetrahydro-2-(1H)-pyrimidinone (DMPU)(7.5 ml) at 0°-5° C. After 5 minutes, ethanethiol (0.66 ml) was added dropwise during 3 minutes. The mixture was maintained at 0°-5° C. for 10 minutes and then heated at 135°-140° C. for 50 minutes. The cooled reaction mixture was diluted with water (15 ml) and then washed with dichloromethane (2×30 ml). The aqueous phase was acidified to pH4 with acetic acid and extracted with diethyl ether (4×30 ml). The ether extracts were dried ($MgSO_4$) and evaporated. The oil obtained was purified by flash column chromatography on silica, eluting with toluene/ethyl acetate/acetic acid (80:20:2, by volume), to give 4(Z)-6-(4-o-hydroxyphenyl-2,2-dimethyl-1,3-dioxan-cis-5-yl)hexenoic acid (A), as a colourless solid (95 mg, 31%), m.p. 85°-89° C.; NMR: 1.6 (7H, m), 1.82 (1H, m), 2.32 (5H, m), 2.7 (1H, m), 3.83 (1H, dd), 4.12 (1H, qq), 5.24 (3H, m), 6.88 (3H, m), 7.17 (2H, m) and 8.47 (1H, s); m/e: 320 (M+).

The preparation of acid B is described as part of Example 7.

EXAMPLES 2-6

Using a similar procedure to that described in Example 1, but starting from the appropriately substituted heterocyclic aldehyde of formula V, the following acids of formula VII were obtained in yields of 10-64%:

| Example | X | Z | m.p. (°C.) | Partial NMR Data |
|---|---|---|---|---|
| 2 | O* | H | oil | 5.75 (1H,s), 6.32 (1H,m), 6.48 (1H,m), 7.02 (4H,m), 7.4 (1H,m) |
| 3 | S* | 5-Br | oil | 5.86 (1H,s), 6.95 (5H,m), 7.18 (1H,m) |
| 4 | S* | 5-$NO_2$ | 150-153 | 5.95 (1H,s), 6.86 |

-continued

| Example | X | Z | m.p. (°C.) | Partial NMR Data |
|---------|-----|-------|-------|----------------------------------|
| 5 | O* | 5-NO₂ | 48–50 | (2H,m), 7.13 (2H,m), 7.32 (1H,m), 7.85 (1H,m) 5.82 (1H,s), 6.82 (3H,m), 7.16 (2H,m), 7.31 (1H,m). |
| 6 | S+ | 5-NO₂ | 39–41 | 5.72 (1H,s), 6.85 (2H,m), 7.12 (2H,m), 7.69 (1H,d), 8.0 (1H,d). |

Note:
*attached at the 2-position of the furan or thiophene moiety.
+attached at the 3-position of the thiophene moiety.

EXAMPLE 7

Sodium hydride (118 mg, 50% w/w dispersion in mineral oil) was added to a stirred suspension of 4(Z)-6-([2,4,5-cis]-2-[3-furyl]-4-o-methoxyphenyl-1,3-dioxan-5-yl)hexenoic acid (152 mg) in 1,3-dimethyl-3,4,5,6-tetrahydro-2(1H)-pyrimidinone (DMPU) (6 ml) maintained at 0°–5° C., after 3 minutes, ethanethiol (0.18 ml) was added and the mixture heated to 95° for 4.5 hours. The cooled mixture was diluted with water (10 ml) and washed with methylene chloride (2×20ml). The aqueous phase was acidified to pH4 with acetic acid and extracted with diethyl ether (4×30 ml). The extracts were dried (MgSO₄) and evaporated. The oil thus obtained was purified by flash column chromatography on silica, eluting with hexane/ethyl acetate/acetic acid (70:30:1, by volume) to give 4(Z)-6-([2,4,5-cis]-2-[3-furyl]-4-o-hydroxyphenyl-1,3-dioxan-5-yl)hexenoic acid as a colourless oil (105mg, 72%); NMR: 1.75 (1H,m), 1.95 (1H,m), 2.3 (4H,m), 2.72 (1H,m), 4.14 (2H,m), 5.37 (3H,m), 5.73 (1H,s), 6.52 (1H,t), 6.9 (3H,m), 7.17 (1H,m), 7.42 (1H,t), : 7.57 (1H,m) and 7.82 (1H,m); m/e 358 (M+)

The starting o-methoxyphenyl compound was obtained as follows:

3-Furancarbaldehyde (0.19 ml) and p-toluene sulphonic acid (5 mg) were added to a solution of 4(Z)-6-(4-o-methoxyphenyl-2,2-dimethyl-1,3-dioxan-cis-5-yl) hexenoic acid (B)(500 mg) in toluene (12 ml). The mixture was stirred and heated under reflux for 1 hour. The cooled reaction mixture was purified by flash column chromatography on silica, eluting with hexane/ethyl acetate/acetic acid (70:30:1, by volume), to give 4(Z)-6-([2,4,5-cis]-2-[3-furyl]-4-o-methoxyphenyl-1,3-dioxan-5-yl)hexenoic acid (261 mg, 47%) as a colourless oil; NMR: 1.63 (1H,m), 1.92 (1H,m), 2.32 (4H,m), 2.57 (1H,m), 3.81 (3H,s), 4.13 (2H,m), 5.34 (3H,m), 5.78 (1H,s), 6.55 (1H,d), 6.93 (2H,m), 7.22 (1H,m), 7.43 (2H,m) and 7.6 (1H,t); m/e 373 (M+).

The starting acid (B) was obtained as follows:

Potassium t-butoxide (12.3 g) was added over 2 minutes to a stirred suspension of (3-carboxypropyl)triphenylphosphonium bromide (23.6 g) in tetrahydrofuran (THF) (230 ml) at 0°–5° C. The mixture was stirred at ambient temperature for 30 minutes and cooled to 0° C. before the addition of (4-o-methoxyphenyl-2,2-dimethyl-1,3-dioxan-cis-5-yl)acetaldehyde (5.9) (obtained as described in Example 13a of European patent application, Publication No.94239) during 5 minutes. The mixture was stirred for 45 minutes and water (50 ml) was added. The solvent was removed by evaporation. The residue was dissolved in water (250 ml). The solution obtained was washed with ethyl acetate (3×100 ml) and acidified to pH 4 with acetic acid. The liberated oil was extracted with ethyl acetate (3×100 ml). The extracts were washed with saturated brine (2×100 ml), dried (MgSO₄) and evaporated to give an oil. The oil was purified by flash column chromatography on silica, eluting with toluene/ethyl acetate/acetic acid (80:20:1, by volume), to give 4(Z)-6-(4-o-methoxyphenyl-2,2-dimethyl-1,3-dioxan-cis-5-yl)hexenoic acid (B) as a colourless solid (6.0 g, 82%) m.p. 92°–96° C.; NMR: 1.65 (8H, m), 2.35 (5H, m), 3.85 (5H, m), 5.28 (3H, m) and 7.1 (4H, m).

EXAMPLE 8

Using a similar procedure to that described in Example 7, but starting from 4(Z)-6-([2,4,5-cis]-4-o-methoxyphenyl-2-[3-thienyl]-1,3-dioxan-5-yl)hexenoic acid, there was obtained, after flash chromotography and elution with hexane/ethyl acetate/acetic acid (70:30:1, by volume), 4(Z)-6-([2,4,5-cis-]-4-o-hydroxy-phenyl-2-[3-thienyl]-1,3-dioxan-5-yl)hexenoic acid as a colourless oil (79%); NMR:1.77 (1H,m), 1.96 (1H,m), 2.35 (4H,m), 2.77 (1H,m), 4.2 (2H,m), 5.38 (3H,m), 5.78 (1H,s), 6.87 (2H,m), 6.93 (1H,m), 7.18 (2H,m), 7.32 (1H,m), 7.47 (1H,m) and 7.86 (1H,m); m/e 375 (M+H)

The starting o-methoxyphenyl compound was obtained using an analogous procedure to that described for the starting material of Example 7, but using 3-thiophenecarbaldehyde in place of 3-furancarbaldehyde There was thus obtained after flash chromatography eluting with hexane/ethyl acetate/acetic acid (75:25:1, by volume), 4(Z)-6-([2,4,5-cis]-4-o-methoxyphenyl-2-[3thienyl]-1,3-dioxan-5-yl)hexanoic acid, as a yellow oil (66%); NMR: 1.68 (1H,m), 1.95 (1H,m), 2.32 (4H,m), 2.58 (1H,m), 3.85 (3H,s), 4.16 (2H,m), 5.35 (3H,m), 5.83 (1H,s), 6.93 (2H,m), 7.28 (3H,m) añd 7.5 (2H,m); m/e 388 (M+).

EXAMPLE 9

Using a similar procedure to that described in Example 1 but using 5-cyano-2-thiophenecarbaldehyde (prepared as described by Vecchi and Malone in J. Org. Chem., 1957, 22,1638), there was obtained 4(2)-6([2,4,5-cis]-2-[5-cyano-2-thienyl]-4-o-hydroxphenyl-1,2-dioxan-5-yl)hexenoic acid as a solid in 27% yield, m.p. 157°–159° C.; microanalysis, found: C, 62.9; H,5.4; N, 3.4%; C₂₁H₂₁NO5 requires: C,63.1; H,5.3; N,3.5%.partial NMR: 5.96(1H,5), 6.82(2H,m), 7.15(4H,m), 7.55(1H,d).

EXAMPLE 10

An illustrative dosage form of a composition of the invention is provided by the following capsule formulation:

|  | mg per capsule |
|---|---|
| Compound X* | 10 |
| Lactose Ph. Eur | 588.5 |
| Magnesium stearate | 1.5 |

The capsules may conveniently be of hard gelatine and are filled in conventional manner. Compound X* is a compound of the invention as defined hereinbefore, for example the compound of Example 4, 8 or 9, or a salt thereof.

| Chemical Formulae of Description | |
|---|---|
| 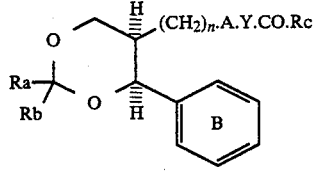 | Z |
| 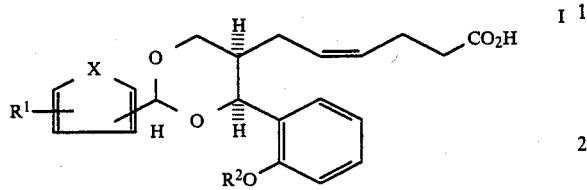 | I |
| | II |
| | III |
| | IV |
| 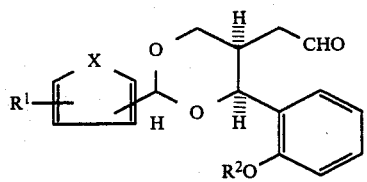 | V |
| 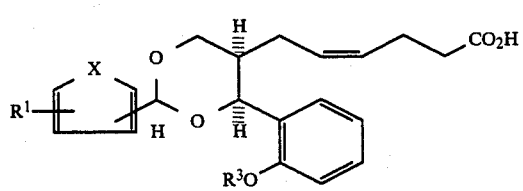 | VI |
| 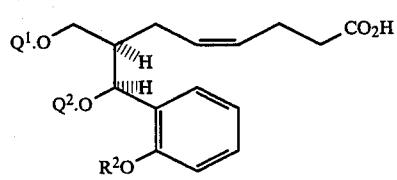 | |
| 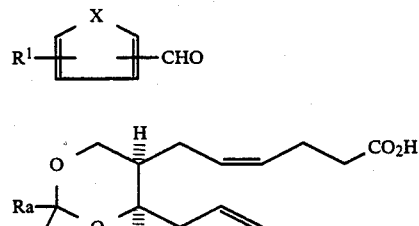 | |
| 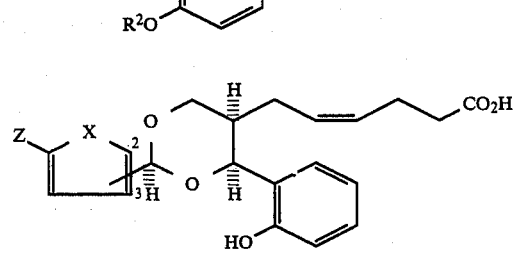 | VII |

Scheme I

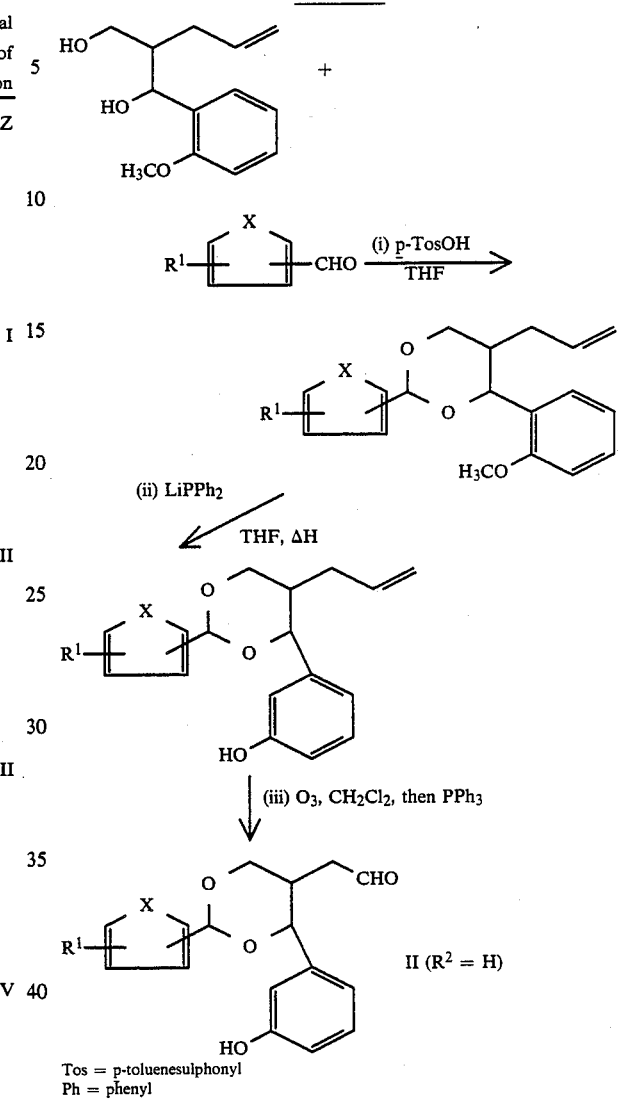

Tos = p-toluenesulphonyl
Ph = phenyl

What is claimed is:

1. A 1,3-dioxane hexenoic acid of the formula I wherein X is oxy or thio, $R^1$ is selected from hydrogen, halogeno, trifluoromethyl, cyano and nitro; $R^2$ is hydrogen; and wherein the groups at positions 2, 4 and 5 of the 1,3-dioxane ring have cis - relative sterochemistry; or a biodegradable ester or a (1-6C)alkanesulphonamide thereof; or a pharmaceutically acceptable salt thereof.

2. A compound as claimed in claim 1 wherein $R^1$ is selected from hydrogen, fluro, chloro, bromo, trifluoromethyl, cyano and nitro.

3. A compound as claimed in claim 1 wherein the heterocyclyl group containing X and bearing the substituent $R^1$ is selected from 2-furyl, 3-furyl, 2-thienyl, 3-thienyl, 5-bromo-2-thienyl, 5-nitro-2-furyl, 5-nitro-2-thienyl, 5-nitro-3-thienyl, 5-bromo-3-thienyl and 5-cyano-2-thienyl.

4. A 1,3-dioxane hexenoic acid of the formula VII

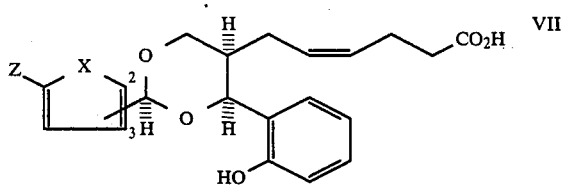

wherein Z is selected from hydrogen, nitro, halogeno and cyano; X is oxy or thio; and the groups at positions 2,4 and 5 of the 1,3-dioxane ring have cis-relative stereochemistry; or a biodegradable ester or a (1–6C)alkanesulphonamide thereof; or a pharmaceutically acceptable salt thereof.

5. A biodegradable ester as claimed in claim 1 selected from (1–4C)alkyl, phenyl and benzyl esters.

6. A (1–6C)alkanesulphonamide as claimed in claim 1 selected from the group consisting of the methanesulphonamide, ethanesulphonamide and 1-methylethanesulphonamide, and the pharmaceutically acceptable salts thereof.

7. A compound selected from 4(Z)-6-([2,4,5-cis]4-o-hydroxyphenyl-2-[5-nitro-2-thienyl]-1,3-dioxan-5-yl)hexenoic acid, 4(Z)-6-([2,4,5-cis]-4-o-hydroxyphenyl-2-[3-thienyl]-1,3-dioxan-5-yl)hexenoic acid, 4(Z)-6-([2,4,5-cis]-2[5-cyano-2-thienyl]-4-o-hydroxyphenyl-1,3-dioxan-5-yl)hexenoic acid, and the pharmaceutically acceptable salts thereof.

8. A salt as claimed in claim 1 selected from the group consisting of alkali metal, alkaline earth metal, aluminum and ammonium salts, and salts with organic amines and quaternary bases forming a physiologically acceptable cation.

9. A pharmaceutical composition which comprises a compound of formula I or VII set out hereinbelow, or a biodegradable ester or a (1–6C)alkanesulphonamide thereof, or a pharmaceutically acceptable salt thereof, as claimed in claim 1 or 4, together with a pharmaceutically acceptable diluent or carrier.

10. A method of antagonising one or more of the actions of thromboxane $A_2$ in a warm-blooded animal requiring such treatment which comprises administering to said animal an effective amount of a compound of the formula I or VII set out hereinbelow, or a biodegradable ester a (1–6C)alkanesulphonamide thereof, or a pharmaceutically acceptable salt thereof, as claimed in claim 1 or 4.

11. A compound of the formula III

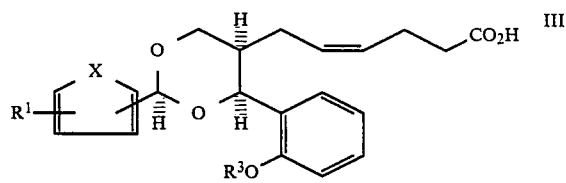

wherein $R^1$ and X have the meanings defined in claim 1 and $R^3$ is (1–4C)alkyl.

* * * * *